United States Patent
Heindl et al.

(10) Patent No.: US 8,129,314 B2
(45) Date of Patent: Mar. 6, 2012

(54) PLANT PROTECTION COMPOSITION ABSORBATES AND PRODUCTS FOR PLANT PROTECTION

(75) Inventors: Frank Heindl, Rodenbach (DE); Claus-Peter Drexel, Neu-Isenburg (DE)

(73) Assignee: Evonik Degussa GmbH, Essen (DE)

( * ) Notice: Subject to any disclaimer, the term of this patent is extended or adjusted under 35 U.S.C. 154(b) by 716 days.

(21) Appl. No.: 11/624,982

(22) Filed: Jan. 19, 2007

(65) Prior Publication Data
US 2007/0191225 A1 Aug. 16, 2007

(51) Int. Cl.
| A01N 25/08 | (2006.01) |
| A01N 25/26 | (2006.01) |
| A01N 25/12 | (2006.01) |
| A01N 25/14 | (2006.01) |
| A01N 25/04 | (2006.01) |
| A01N 25/16 | (2006.01) |

(52) U.S. Cl. ..................... 504/367; 504/101
(58) Field of Classification Search ............ 504/101, 504/367
See application file for complete search history.

(56) References Cited

U.S. PATENT DOCUMENTS

| 6,960,251 B2 * | 11/2005 | Uhrlandt et al. ............ 106/482 |
| 7,097,818 B2 | 8/2006 | Lindner et al. |
| 2003/0003040 A1 | 1/2003 | Lindner et al. |
| 2006/0017038 A1 * | 1/2006 | Hasenzahl et al. ............ 252/2 |
| 2006/0229210 A1 * | 10/2006 | Neugebauer et al. ......... 504/367 |

FOREIGN PATENT DOCUMENTS
| EP | 1 488 697 | 12/2004 |
| WO | WO 99/17868 | 4/1999 |

OTHER PUBLICATIONS

European Search Report issued Aug. 18, 2011, in EP 06 126 845, filed Dec. 21, 2006.

* cited by examiner

*Primary Examiner* — Anoop Singh
*Assistant Examiner* — Courtney Brown
(74) *Attorney, Agent, or Firm* — Oblon, Spivak, McClelland, Maier & Neustadt, L.L.P.

(57) ABSTRACT

Absorbates having a high loading of particular substances for use in plant protection compositions, the use of a special process for the preparation of the absorbates and products for plant protection comprising the absorbates.

30 Claims, 2 Drawing Sheets

PLANT PROTECTION COMPOSITION ABSORBATES AND PRODUCTS FOR PLANT PROTECTION

BACKGROUND OF THE INVENTION

1. Field of the Invention

The present invention relates to novel absorbates with a special composition, in particular a high loading of particular substances for use in plant protection compositions, the use of a special process for the preparation of the absorbates and products for plant protection comprising the absorbates.

2. Description of the Related Art

In the field of products for plant protection, a distinction is made between solid and liquid formulation types. In the field of solid formulations, liquid or meltable active substances, together with auxiliaries (for example, surfactants and disintegrating agents), are attached to carrier materials. With solid active substances, the carrier materials serve firstly as fillers. With liquid or low melting point active substances the carriers serve to absorb the liquid or low melting point active substances. Superficially dry absorbates are obtainable which are easy to handle and which maybe marketed either directly as powders (WP, wettable powder) or, processed, as granules/extrudates (WG, water dispersible granules).

In the case of WGs, a pre-prepared absorbate powder may be converted to a granule form or the product components maybe formed directly (for example, by spray drying). A possible preparation of WGs by direct spray drying of a dispersion of silica, active substance and additional auxiliaries is disclosed, for example, in U.S. Pat. No. 6,869,914.

In particular with liquid or low melting point active substances and auxiliaries for plant protection compositions, subsequently referred to as "particular substances for use in plant protection compositions", it is impossible with the processes known to date to prepare absorbates with a desired high content of particular substances for use in plant protection compositions. Thus, using conventional processes, absorbates with satisfactory flowability can be prepared only up to 65% by weight based on the total weight of the absorbate (based on a liquid density of 1.00 g/ml).

In mechanical absorption processes, such as, for example, simple mixing of the components, a very broad distribution in the size of the agglomerates of the absorbates is to be expected in the region of the limit load of the silica. This tends to greatly reduce the flowability of the resulting products and aggravates further handling (metering, and the like). In addition, in conventional mixing processes it is difficult to avoid compacting agglomeration. Such compacting agglomerates are undesirable, for example when the product is used as WP, since they have a negative effect on the desired good disintegration behavior on redispersing in water.

Additional disadvantages of the absorbates of the state of the art are a sometimes expensive preparation process and in particular a high proportion of expensive carrier materials, which also include carrier material silicas. In products for plant protection in particular, which are produced and sold in very large amounts, even a small reduction in the amounts of the carrier materials used would already be tremendously advantageous economically and also ecologically.

SUMMARY OF THE INVENTION

It is accordingly an object of the present invention to provide novel absorbates which do not exhibit at least some of the disadvantages of the absorbates of the state of the art or exhibit them only to a reduced extent and which make it possible to prepare novel products for plant protection.

It is a further object of the invention to provide an absorbate including a carrier material and a plant protection material.

It is a further object of the invention to provide a process for making absorbates.

It is a further object of the invention to provide a process of applying the absorbates onto plants for plant protection.

This and other objects of the invention are achieved by the absorbates and products for plant protection defined more fully in the claims, the description and the examples, and also the process for the preparation thereof more fully defined there.

DETAILED DESCRIPTION OF THE INVENTION

Figure 1:
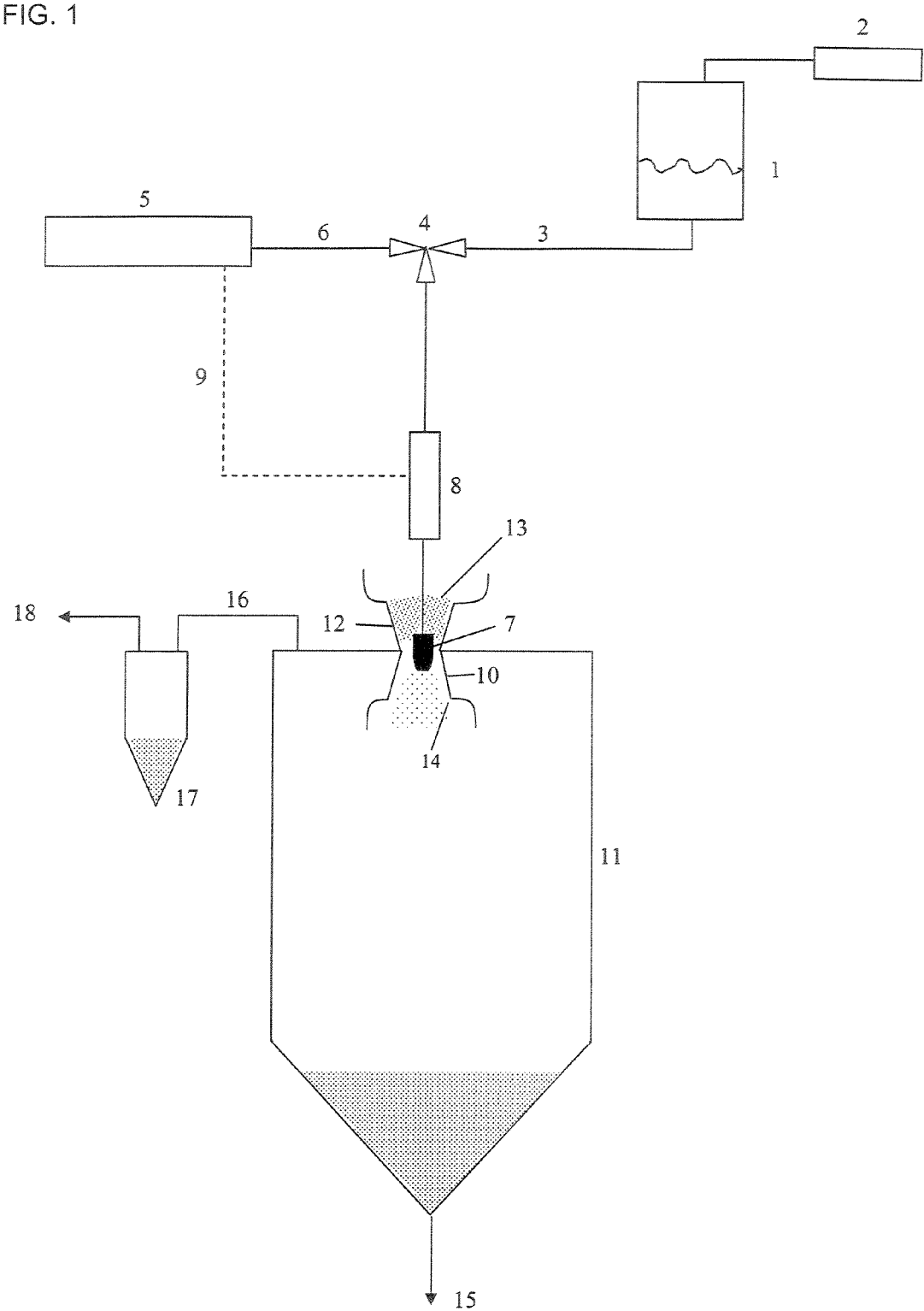
FIG. 1 shows an embodiment of the invention including an autoclave.

It has been found, surprisingly, that it is possible, by the use of a special process for the absorption of liquids on carrier materials in combination with the selection of special carrier materials, to prepare absorbates with a content of particular substances for use in plant protection compositions of at least 70%, based on the total weight of the absorbates and on a liquid density of 1.00 g/ml. In addition to the high loading, it is also possible, by the use of special carrier materials, to achieve a particularly good, i.e. complete or to the greatest possible extent complete, desorption of the particular substances from the carried after redispersing the absorbates in water.

The absorbates according to the invention have the advantage that they, in comparison to absorbates of the state of the art, exhibit a considerably higher loading of absorbed particular substances for use in plant protection compositions and yet are superficially dry, resistant to compaction under pressure, and flow well.

Furthermore, an advantageously low cost for the absorbates can be achieved by the use of special carrier materials like precipitated silicas in combination with the high loading. In addition, the requirements and conditions of environmental protection may be met because the carrier materials are completely harmless ecologically.

A particular advantage of the use of precipitated silicas, pyrogenic silicas and silica gels as carrier materials has proven to be that the physicochemical properties thereof can be purposefully adapted to the particular substance for use in plant protection compositions to be absorbed or a mixture of substances comprising a particular substance for use in plant protection compositions. In particular, the inventors have found out that precipitation silicas, pyrogenic silicas and silica gels with a special pore distribution, when used in combination with the preparation process according to the invention, provide absorbates that exhibit both a high loading and excellent desorption properties. Precipitated silicas with a special pore distribution have proven to be particularly advantageous in this regard.

An additional advantage of the absorbates according to the invention is that they can also be prepared with particular substances for use in plant protection compositions which hitherto could only insufficiently be brought into the form of absorbates. The reason is that no high drying temperatures are necessary due to the use of a Concentrated Powder Form (CPF) process.

Finally, the absorbates according to the invention exhibit an advantageous agglomerate size distribution.

One embodiment of the invention includes absorbates, that comprise at least one carrier material chosen from the group consisting of precipitated silicas, pyrogenic silicas, silica gels, natural clays, modified natural clays and diatomaceous earths, and at least one particular substance for use in plant protection compositions or a mixture of substances comprising at least one particular substance for use in plant protection compositions, and that the proportion of the particular substance for use in plant protection compositions or, in mixtures of at least two particular substances for use in plant protection compositions, the total amount of the particular substances for use in plant protection compositions, $X_{stand.}$, is 70% to 99%.

Another embodiment of the invention includes products for plant protection comprising at least one absorbate according to the invention, and the use of an absorbate according to the invention for the preparation of products for plant protection.

The invention further includes the use of at least one precipitated silica, pyrogenic silica, silica gel, natural clay, modified natural clay and diatomaceous earth for the preparation of absorbates loaded with particular substances for use in plant protection compositions or mixtures of at least two particular substances for use in plant protection compositions, the total amount of the particular substances for use in plant protection compositions being from $X_{stand.}$=70% to 99%.

The use of a process comprising at least the following stages is also included in the invention:

providing a liquid, comprising at least one liquid or molten particular substance for use in plant protection compositions and/or at least one liquid or molten mixture of substances comprising at least one particular substance for use in plant protection compositions, in a feed vessel, mixing and/or partly dissolving a gas, preferably under elevated pressure, particularly preferably in the super-critical condition, in particular $CO_2$ at a pressure p>73.83 bar and at a temperature T>31.04° C., in the liquid, preferably in a mixer and/or pressurized vessel, feeding the liquid/gas solution/melt to an expansion element, conveying the liquid/gas solution or the liquid/gas melt through an expansion element to expand the liquid/gas solution or the liquid/gas melt, adding at least one solid pulverulent carrier material to the expanded liquid/gas solution or liquid/gas melt.

Another embodiment of the invention includes a process comprising the use of the abovementioned process for the preparation of absorbates charged with particular substances for use in plant protection compositions and the subsequent further processing of these absorbates to give products for plant protection.

The term "particular substances for use in plant protection compositions" is understood to mean, within the meaning of the present invention, liquid or low melting point (e.g., melting point<=80° C.) active substances and/or auxiliaries for plant protection compositions.

Active substances for plant protection compositions are substances which have a direct or indirect biological activity against attack by pests on or diseases of plants or which affect the metabolism or the growth of the plants. These include the active substances which are suitable for preventing, controlling or combating attack by pests and/or for preventing, regulating and/or minimizing damage to or diseases of plants, wood or wood products which can occur during the growth, production, processing, storage, transportation or marketing and/or for regulating, minimizing or preventing the effects of insects, acarids or other pests on working animals which are fed with the plants. This includes active substances which are certainly for use as insect or plant growth regulators and also defoliants, desiccants, agents for regulating, weakening or preventing the premature putrefaction of fruit and substances for application to cereals, either before or after harvesting, in order to protect the harvested crop from damage during storage and transportation. Further details on the definition, nomenclature and characterization of active substances for plant protection compositions can be taken from the manual "Pesticide Specifications," Manual on Development and Use of FAO and WHO Specifications for Pesticides, published by the World Health Organization (WHO) and Food and Agriculture Organization of the United States, Rome, 2002, ISBN 92-5-104857-6. The entire contents of this publication are hereby incorporated by reference herein.

The active substances for plant protection compositions are preferably liquid or low melting point active substances, such as can be taken, for example, from the CIPAC manual H, "Analysis of Technical and Formulated Pesticides", published by the Collaborative International Pesticides Analytical Council Limited, 1998, ISBN 0902951130. The contents of this document are hereby explicitly incorporated by reference herein.

The term "auxiliaries for plant protection compositions" is understood as meaning, within the meaning of the present invention, substances which are used to emulsify or disperse the active substance or which make possible the problem-free application of the formulation. Examples of auxiliaries for plant protection compositions can be taken from EP 1 319 336 A1. These auxiliaries are preferably liquid auxiliaries, low-melting-point auxiliaries or auxiliaries soluble in the active substance. The following are particularly preferred as auxiliaries:

surfactants according to EP 1 319 336 A1, paragraphs 0030 and 0038 to 0041 buffers according to EP 1 319 336 A1, paragraph 0048 antifoaming agents according to EP 1 319 336 A1, paragraph 0043

The entire contents of EP 1 319 336 A1 and in particular the paragraphs explicitly mentioned above are incorporated herein by reference.

The content of particular substance for use in plant protection compositions is determined in the following way. Porous structures absorb always with reference to volume. Consequently, the use of liquids of higher density generally results in higher loadings by weight in comparison to liquids of low density. In order to be able to give comparable details, the proportion of particular substance for use in plant protection compositions is accordingly given, in the context of the present invention, as concentration by weight, based on a liquid density of 1.00 g/ml and the total weight of the absorbate.

The standardization with regard to a liquid density of 1.00 g/ml is carried out according to formula (I):

$$X_{stand.} = \frac{100}{\rho_l^* \left( \frac{100}{X_{before}} - 1 \right) + 1} \quad \text{formula (I)}$$

with $X_{stand.}$=concentration by weight standardized with regard to a liquid density of 1.00 g/ml, given in %, $X_{before}$=concentration by weight before standardization, in %, $\rho_l$=density of the absorbed particular substance for use in plant protection compositions or of the mixture of particular substances for use in plant protection compositions, in g/ml.

The loading by weight before the standardization is calculated according to formula (II) as follows:

$$X_{before} = \frac{W_{l\,abs.}}{W_{abs.total}} * 100\% \quad \text{formula (II)}$$

with $W_{l\,abs.}$=weight of the absorbed particular substance for use in plant protection compositions, in g, $W_{abs.\,total}$=total weight of the absorbate, in g.

As already mentioned above, the standardization is necessary since, without considering the density of the absorbed liquid, no statement can be made with regard to how heavily loaded the carrier material really is. Thus, the carrier in an absorbate in which 50 g of carrier material has absorbed 50 g of a liquid with a density of 1.00 g/ml is much more heavily loaded (it has to absorb more liquid volume) than a carrier in an absorbate in which 50 g of carrier material has absorbed 50 g of a liquid with a density of 1.30 g/ml. $X_{stand.}$ accordingly describes the concentration by weight of an absorbate of a liquid with a density 1 g/cm³ which comprise the same volume of liquid as the actual absorbate. The consequence of this is that, for a liquid density of $\rho l=1$, the standardized loading by weight $X_{stand.}$ is the same as the loading by weight before the standardization $X_{before}$. However, if a liquid with a density of 1.30 g/ml is absorbed, the standardized loading by weight $X_{stand.}$ is thus smaller than the loading by weight before the standardization $X_{before}$. In this case, the circumstance is accordingly taken into account that the carrier, because of the liquid density of 1.30 g/ml, has to absorb a smaller volume of liquid and accordingly a higher loading potential is by and large available with this liquid.

The following calculation examples should show this more clearly:

Calculation Example 1

A 70% absorbate of a particular liquid for use in plant protection compositions with a density of 1.23 g/ml corresponds, after standardization with regard to a liquid density of 1.00 g/ml, to an absorbate with a loading by weight of $X_{stand.}$=100/(1.23*((100/70)−1)+1)=65.48%.

Calculation Example 2

116.7 g of a liquid with a density of 1.30 g/ml are absorbed on 50 g of silica. This gives $X_{before}$=116.7/(116.7+50)*100=70%

This in turn corresponds to a standardized loading of:

$X_{stand.}$=100/(1.30*((100/70)−1)+1)=64.22%.

The absorbates according to the invention, loaded with particular substances for use in plant protection compositions, are distinguished in that at least one carrier material chosen from the group consisting of precipitated silicas, pyrogenic silicas, silica gels, natural clays, modified natural clays and diatomaceous earths is present, at least one particular substance for use in plant protection compositions or a mixture of substances comprising at least one particular substance for use in plant protection compositions is present as active substance, and the proportion of particular substances for use in plant protection compositions or, in mixtures of at least two particular substances for use in plant protection compositions, the total amount of particular substances for use in plant protection compositions is from $X_{stand.}$=70% by weight to 99% by weight.

The carrier material preferably exhibits a tapped density of less than 200 g/l, very particularly preferably <150 g/l and in particular <100 g/l. The adsorbates according to the invention particularly preferably comprise at least one precipitated silica, pyrogenic silica or silica gel as carrier material.

In a preferred embodiment of the present invention, the carrier material exhibits a proportion of the micropore volume, based on the total pore volume, of less than or equal to 10% by volume, preferably less than or equal to 7% by volume, particularly preferably less than or equal to 5% by volume and in particular 0.01 to 5% by volume, and/or a DBP (di-butyl-phthalate) absorption of greater than or equal to 150 g/100 g, preferably between 200 and 450 g/100 g.

In a preferred version of this embodiment, the carrier material is a precipitated silica, a pyrogenic silica or a silica gel and particularly preferably a precipitated silica.

The surface of the carrier materials, in particular of silicas and silica gels, can be treated with a surface-modifying agent. Hydrophobic or partially hydrophobic carriers, e.g., may consequently be concerned.

Contrary to the teaching of the state of the art, such as, for example, WO 99/17868, the inventors of the present invention have recognized that it is important, for the preparation of absorbates with a high content of suitable substances for use in plant protection compositions which simultaneously exhibit good desorption properties, for the carrier materials used to exhibit a particular pore volume distribution, i.e. a low proportion of micropore volume. Otherwise, it may happen that the carrier materials indeed absorb a high amount of active substance but that this active substance is only re-released very incompletely or very slowly.

The amount $X_{stand.}$ of particular substances for use in plant protection compositions or, in mixtures of at least two particular substances for use in plant protection compositions, the total amount of particular substances for use in plant protection compositions is preferably between 70 and 95%, particularly preferably between 75 and 95% and in particular between 81 and 90%.

It is preferable for the absorbates according to the invention to comprise only the carrier material and the particular substance(s) for use in plant protection compositions.

The absorbates according to the invention preferably exist in the form of
- solid formulations for direct use, such as dustable powders (DP), powders for dry seed treatment (DS), granules (GR) or tablets for direct application (DT),
- solid formulations for dispersion, such as wettable powders (WP), water dispersible powders for seed treatment (WS), water dispersible granules (WG), water dispersible tablets (WT), emulsifiable granules (EG) or emulsifiable powders (EP),
- solid formulations for dissolution before application, such as water soluble powders (SP), water soluble powders for seed treatment (SS), water soluble granules (SG) or water soluble tablets (ST).

WG or WP formulations are particularly preferred.

The abovementioned formulation forms and in particular the abbreviations used correspond to the internationally recognized usage. Details can be found in the manual "Pesticide Specifications," Manual on Development and Use of FAO and WHO Specifications for Pesticides, published by the World Health Organization (WHO) and the Food and Agriculture Organization of the United States, Rome, 2002, ISBN 92-5-104857-6, Appendix E. The entire contents of this publication and in particular of Appendix E are incorporated herein by reference.

A process can be used for the preparation of the absorbates according to the invention which comprises at least the following stages:
- providing a liquid, comprising at least one liquid or molten particular substance for use in plant protection compositions and/or at least one liquid or molten mixture of substances comprising at least one particular substance for use in plant protection compositions, in a feed vessel,
- mixing and/or partly dissolving a gas, preferably under elevated pressure, particularly preferably in the supercritical condition, in particular $CO_2$ at a pressure p>73.83 bar and at a temperature T>31.04° C., in the liquid, preferably in a mixer and/or pressurized vessel,
- feeding the liquid/gas solution/melt to an expansion element,
- conveying the liquid/gas solution or the liquid/gas melt through an expansion element to expand the liquid/gas solution or the liquid/gas melt,
- adding at least one solid pulverulent carrier material to the expanded liquid/gas solution or liquid/gas melt.

The substances defined earlier in the description of the absorbates according to the invention can be used as carriers or as particular substance or substances for use in plant protection compositions.

Different gases can be used in the process which can be used according to the invention.

In principle, use may be made, as gas, of any gas which is satisfactorily dissolved in the liquid, to be sprayed, comprising at least one liquid or molten particular substance for use in plant protection compositions and/or at least one liquid or molten mixture of substances comprising at least one particular substance for use in plant protection compositions. Use may be made, as gas, for example, of carbon dioxide, a hydrocarbon, in particular methane, ethane, propane, butane, ethene, propene or a halogenated hydrocarbon, an ether, an inert gas, in particular nitrogen, helium or argon, a gaseous oxide, in particular dinitrogen oxide or sulphur dioxide, and ammonia. A mixture of two or more of the abovementioned gases can also be used.

The dissolution of the gas or the mixing of the gas with the liquid comprising at least one liquid or molten particular substance for use in plant protection compositions and/or at least one liquid or molten mixture of substances comprising at least one particular substance for use in plant protection compositions can be carried out in different ways. Thus, it is possible to carry out the dissolution or the mixing in a pressure-resistant, optionally heatable, feed vessel, e.g. a suitable autoclave. However, it is also possible to carry out the mixing or dissolution in an optionally heatable mixing assembly, in particular a static mixer, which is connected downstream to an optionally heatable, pressure-resistant, feed vessel.

In a preferred embodiment, the use of a pressure-resistant, optionally heatable, feed vessel is avoided. Instead, the liquid comprising at least one liquid or molten particular substance for use in plant protection compositions and/or at least one liquid or molten mixture of substances comprising at least one particular substance for use in plant protection compositions is placed in an optionally heatable feed vessel of any dimensions and fed by means of a suitable pump to a suitable mixing assembly, e.g. a static mixer, where the liquid is mixed with a gas or the gas is dissolved in the liquid. The liquid/gas mixture or the liquid/gas solution/melt can subsequently be fed directly to an expansion element.

Combinations of the processes described above are likewise possible.

The mixing or dissolution of the gas in the liquid is preferably carried out at elevated pressure.

The elevated pressure under which the gas is dissolved in the liquid substance or mixture of substances can lie in the range from 5 bar to 800 bar, is, however, preferably 10 bar to 350 bar and particularly preferably lies in the range from 20 bar to 250 bar.

Preferably, the dissolution of the gas in the liquid substance or mixture of substances is accelerated by mixing the gas with the liquid substance or mixture of substances. This mixing can be carried out, for example, by shaking or rolling a vessel in which the gas and the liquid are brought together. For example, this can be a pressurized vessel into which the liquid to be atomized is introduced. Alternatively, the liquid/melt can be stirred with a gas during and/or after the operation in which they are brought together. Yet another possible way of achieving good intermixing of the gas with the liquid/melt to be atomized consists in pumping over the liquid/melt and/or the gas phase in different vessels or in recirculating the liquid/melt and/or the gas phase, i.e. pumping out from the pressurized vessel and refeeding the pressurized vessel in the region of the other phase each time. A particularly preferred possibility is the use of a static mixer, the liquid/melt and the gas phase very particularly preferably being brought together only directly in the mixer and/or at the inlet of the mixer. The abovementioned embodiments can also be combined.

It may be necessary for different parts of the plant to have to be able to be heated externally in order to bring the particular substance for use in plant protection compositions to the liquid form or to keep in this form. It may be necessary for this to provide, e.g. feed vessels, supply lines, mixers, expansion element and valves, with suitable heating capabilities. Thus, for example, it may be necessary for the supply lines between the feed vessel and the mixer and/or between the mixer and the expansion element and/or the feed vessel and the expansion element, and/or the feed vessel itself and/or the mixer and/or the expansion element to have to be heated in order to keep in the liquid condition the liquid comprising at least one liquid or molten particular substance for use in plant protection compositions and/or at least one liquid or molten mixture of substances comprising at least one particular substance for use in plant protection compositions or the mixture of the said liquid and the gas. In this connection, the operation is preferably carried out with temperatures of up to 80° C.

Use may be made in the process according to the invention, as expansion element, of any device which makes possible a satisfactorily fast expansion of the liquid/gas solution. Use is preferably made, as expansion element, of a nozzle, a diffuser, a capillary, an orifice, a valve or a combination of the abovementioned expansion elements.

In the expansion of the liquid/gas solution/melt, the temperature can fall below the solidification point of the substance or mixture of substances. However, this is not absolutely necessary in order to obtain the desired pulverulent product. In a number of application cases, it has certainly proved to be convenient, on expanding the liquid/gas solution, to achieve a temperature which is at least in the vicinity of the solidification point of the substance or mixture of substances.

It is important, in the process according to the invention, for the solid pulverulent carrier material added to be mixed with the liquid/gas solution/melt or, according to where the pulverulent auxiliary is fed in, with the liquid to be atomized comprising at least one liquid or molten particular substance for use in plant protection compositions and/or at least one liquid or molten mixture of substances comprising at least one particular substance for use in plant protection compositions.

Various possibilities are available for achieving good intermixing of the carrier material with the liquid/gas solution/melt or the liquid to be atomized comprising at least one liquid or molten particular substance for use in plant protection compositions and/or at least one liquid or molten mixture of substances comprising at least one particular substance for use in plant protection compositions. Thus, the pulverulent carrier material can, for example, be metered in at the point where the liquid/gas solution/melt emerges from the expansion element, thus at or shortly before the expansion point. The carrier material is then entrained in the free jet formed after the expansion point, the considerable and fast expansion in volume of the gas present in the liquid/gas solution/melt ensuring extremely intensive vortexing and mixing of the carrier with the liquid to be atomized comprising at least one liquid or molten particular substance for use in plant protection compositions and/or at least one liquid or molten mixture of substances comprising at least one particular substance for use in plant protection compositions.

According to another embodiment of the process according to the invention, the carrier is fed in in such a way that it surrounds in annular fashion, in the region of the outlet, the stream of substance emerging from the expansion element. This can, e.g., be carried out with a ring nozzle, so that the free jet emerging from the expansion element is at least partially encased by the carrier material. The encasing of the free jet with the carrier furthermore ensures that, just after emergence from the expansion element, droplets of liquid possibly still present cannot be deposited on a surrounding wall but are entrained.

It may be sensible to feed the stream of substance emerging from the expansion element and the carrier to a diffuser in order to be able to control the enlargement in cross section of the free jet. Furthermore, one or more flow separation edges can additionally, with the vortexings produced there, bring about even more intensive intermixing between the free jet and the carrier.

In a preferred embodiment of the process according to the invention, the expansion of the liquid/gas solution/melt is carried out in a spray tower. The carrier to be added can then, for example, be transported to the spray tower by means of methods known to a person skilled in the art, e.g. by means of a screw conveyor or pneumatic conveyance, and metered in at the desired point.

In preferred embodiments of the process according to the invention, additional gas, which can be described as "excess gas", is added additionally to the gas which is already dissolved in the liquid comprising at least one liquid or molten particular substance for use in plant protection compositions and/or at least one liquid or molten mixture of substances comprising at least one particular substance for use in plant protection compositions. This can be carried out particularly advantageously in the region of the expansion element. With this excess gas, the temperature reached in the expansion operation can be adjusted more independently. It is necessary neither for the liquid/gas solution/melt to be essentially saturated with the gas nor, for example, for a relatively high pressure to be chosen in order to achieve a gas concentration in the liquid sufficiently great for the desired cooling down. Rather, it is possible to bring about the desired cooling down in the region of the expansion point to a large extent by the rapid expansion of the excess gas additionally supplied. In addition, the possibility arises of choosing, as excess gas, a gas which is different from the gas dissolved in the liquid. For example, the excess gas can be chosen with regard to the biggest possible lowering in temperature, while the gas to be dissolved in the liquid is decided upon according to other standpoints. In addition to better cooling down in the region of the expansion point, the excess gas also results in an even better intermixing or vortexing after the emergence of the stream of substance from the expansion element and accordingly in even smaller powder particles.

Various possibilities exist with regard to the introduction of the excess gas. According to one embodiment of the process according to the invention, the excess gas is charged to the liquid/gas solution/melt between the pressurized vessel and the expansion element, in particular just before the expansion point. In this connection, a static mixer, for example, can be inserted for better mixing with the liquid/gas solution/melt.

According to another embodiment, the liquid/gas solution/melt and additionally introduced excess gas are expanded together with one another in the expansion element by means of a twin-substance nozzle. In this embodiment, the excess gas is thus not added to the liquid/gas solution/melt but is fed directly to the expansion point, so that the liquid/gas solution/melt and the pure excess gas are expanded simultaneously. The twin-substance nozzle can, for example, be such that the liquid/gas solution/melt emerges through a central channel, while the excess gas emerges through a ring channel which surrounds the central channel coaxially.

According to yet another embodiment, the excess gas is fed together with the solid pulverulent auxiliary to the solution or to the substance or mixture of substances.

The process according to the invention can be operated both continuously and batchwise. For continuous operation, it may be necessary to provide the receiver, e.g. spray tower, for the absorbates according to the invention with a suitable device for continuous feeding of the absorbates according to the invention. Suitable techniques for this, e.g. screw conveyors or star feeders, are known to a person skilled in the art.

As already intimated earlier, several effective embodiments of the process according to the invention are possible. FIG. 1 shows a possible embodiment in which an autoclave is used for mixing or dissolving the gas with/in the liquid comprising at least one liquid or molten particular substance for use in plant protection compositions and/or at least one liquid or molten mixture of substances comprising at least one particular substance for use in plant protection compositions.

FIG. 1 shows, as pressurized vessel, an autoclave 1 which is charged with the liquid to be atomized comprising at least one liquid or molten particular substance for use in plant protection compositions and/or at least one liquid or molten mixture of substances comprising at least one particular substance for use in plant protection compositions. Subsequently, through suitable measures, for example by moving the autoclave 1 or the autoclave contents (e.g., by stirring or recycling), a chosen gas is dissolved under pressure in the liquid introduced. The gas chosen is fed in in a conventional way and is not represented in the figure. To accelerate the dissolution of gas in the liquid to be atomized, the liquid and the gas to be dissolved therein can optionally be conveyed cocurrently through a static mixer 2 and can subsequently be introduced into the autoclave 1. Depending on the type of gas chosen and depending on the pressure chosen and the temperature, gas concentrations between 1 and 90% by weight, preferably 5 to 50% by weight and in particular 10 to 40% by weight can be achieved in the liquid phase. The temperature is expediently in the region of room or ambient temperature. However, with high viscous substances or mixtures of substances, a higher temperature may even be required. It is essential for the liquid to be atomized comprising at least one liquid or molten particular substance for use in plant protection compositions and/or at least one liquid or molten mixture of substances comprising at least one particular substance for use in plant protection compositions to be present in the pressurized vessel as liquid or suspension or melt.

The liquid/gas solution present in autoclave 1 after the dissolution of the gas is fed to a three-way valve 4 via a line 3. Additional gas, "excess gas", is fed to the three-way valve 4 from a gas container 5 via a line 6. The excess gas can be a different gas from that dissolved in the liquid.

The liquid/gas solution and the excess gas introduced are led from the three-way valve 4 to an expansion element, which here is a high pressure nozzle 7. An additional static mixer 8 can be inserted between the high pressure nozzle 7 and the three-way valve 4 in order to improve the incorporation of the excess gas in the liquid/gas solution. However, it is also possible to convey the contents of the autoclave 1 and the excess gas, via the line 9, directly in each case to the static mixer 8 and only there to intermix. The high pressure nozzle 7 is arranged at the narrowest point of a diffuser 10, which is mounted in the lid of a spray tower 11. A solid pulverulent carrier material 13 is fed in continuously via a feed hopper 12, as long as the liquid/gas solution/melt and the excess gas are flowing out of the high pressure nozzle 7. An annular passage, which first narrows and then again widens and through which the auxiliary 13 introduced flows, is formed between the high pressure nozzle 7 and the inner wall of the feed hopper 12 or of the diffuser 10. The auxiliary thus surrounds in annular fashion the stream of substance flowing out of the high pressure nozzle 7. The conveying of the auxiliary 13 into the feed hopper 12 can be carried out using known methods, for example using pneumatic conveyance, through vibrating bars, using a screw feeder or a star feeder, or the like.

The large increase in volume of the gas present in the liquid/gas solution/melt and also of the excess gas additionally introduced after emergence from the high pressure nozzle 7 results in great turbulence and accordingly in good intermixing of the auxiliary with the stream of substance emerging from the high pressure nozzle 7. In the exemplary embodiment shown, a flow separation edge 14 present in the diffuser further increases the turbulence.

The large reduction in temperature which accompanies the expansion of the gas dissolved in the liquid and also of the excess gas ensures, together with the high turbulence mentioned, such a rapid and intensive intermixing with the auxiliary that the desired pulverulent final product is already obtained with a spray tower height of only 1 m. The powder accumulates in the lower part of the spray tower 11 and can be withdrawn conventionally at the outlet 15, optionally continuously or batchwise.

The gas dissolved in the liquid and also the excess gas separate, after emergence from the high pressure nozzle 7, from the substance or mixture of substances to be atomized. In the exemplary embodiment shown, the gas thus released is drawn off in the upper region of the spray tower 11 through a line 16. Discharge of fine particles through the line 16 is prevented by the settling zone present between the diffuser 10 and the inner wall of the spray tower. A fine part of atomized product nevertheless possibly present in the gas drawn off can be removed from the gas stream in a conventional fashion, e.g. using a cyclone 17, before an extraction fan indicated with 18.

Details of the process described above can be found in WO 99/17868. The entire contents of WO 99/17868 are hereby explicitly incorporated by reference herein.

Figure 2:
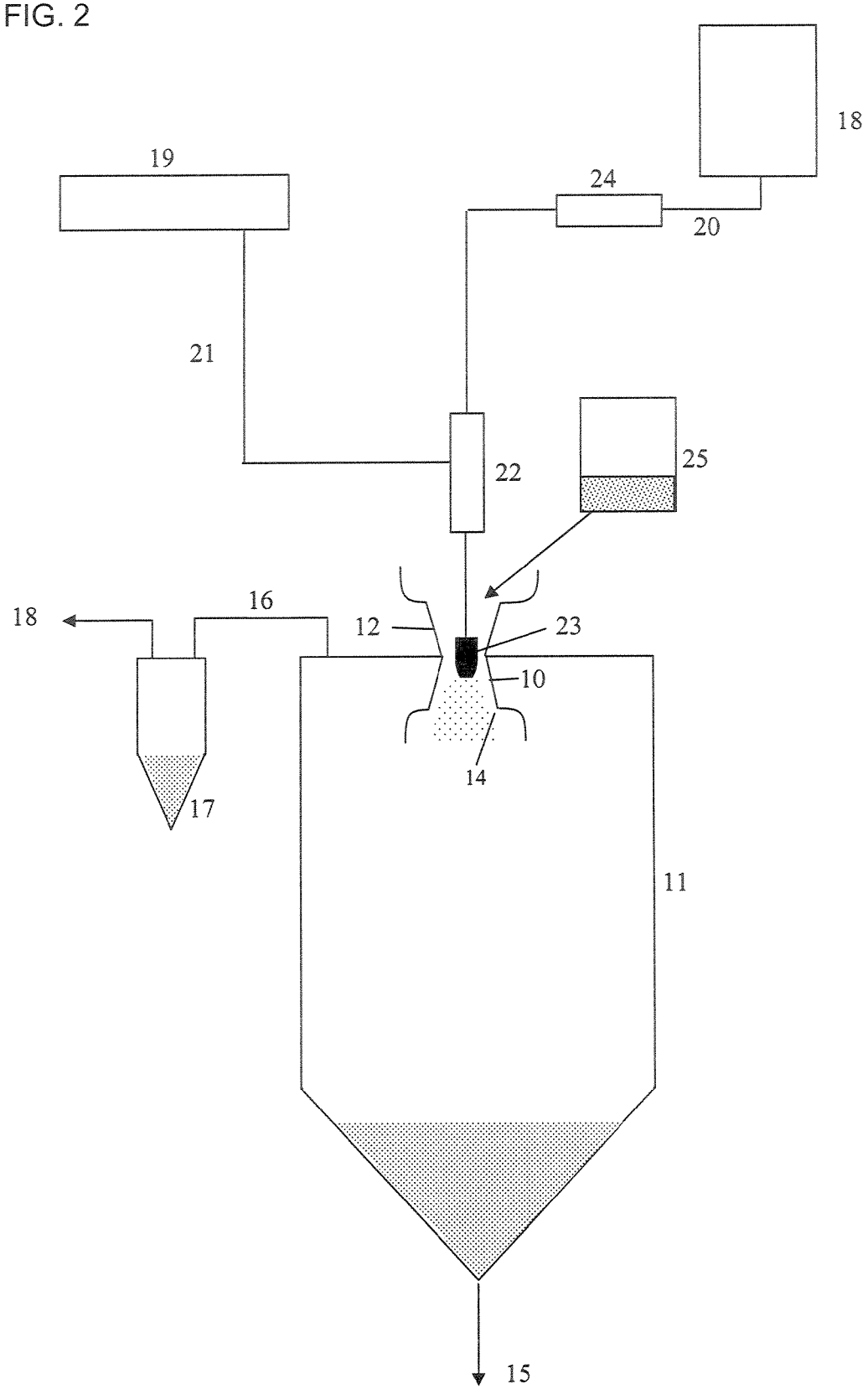
FIG. 2 shows an embodiment of the invention without an autoclave.

An additional, particularly preferred, embodiment of the process according to the invention is represented in FIG. 2.

The process according to FIG. 2 differs from the process according to FIG. 1 in that the use of an autoclave is avoided. Instead, the liquid comprising at least one liquid or molten particular substance for use in plant protection compositions and/or at least one liquid or molten mixture of substances comprising at least one particular substance for use in plant protection compositions is fed from the vessel 18 and the gas is fed from the vessel 19 via the lines 20 and 21 directly to a suitable, e.g. static, mixer 22 and there intensively mixed with one another. The liquid/gas mixture is then directly fed from the mixer 22 to the expansion element 23. This embodiment is spared the use of an expensive high pressure vessel (autoclave) and can moreover result in a reduction in the amount of the gas used. Furthermore, the process is optimized by replacing a time consuming equilibration in the autoclave, as necessary in the process according to FIG. 1, by a faster intermixing in the mixer 22.

The liquid comprising at least one liquid or molten particular substance for use in plant protection compositions and/or at least one liquid or molten mixture of substances comprising at least one particular substance for use in plant protection compositions can, in the process according to FIG. 2, be introduced into a simple, optionally heatable, feed vessel of any size (vessel 18). This vessel 18 does not have to be pressure resistant. The liquid from the feed vessel 18 can be fed to the mixer 22 by means of a suitable pump 24, e.g. a diaphragm metering pump, or pneumatically, there mixed with the gas and, subsequently, fed to the expansion element 23. The expansion element 23 and the feeding of the carrier material are generally employed as described in FIG. 1. In the embodiment according to FIG. 2, the spray tower can be provided with the capability of discharging 15 the absorbates according to the invention continuously or batchwise. The absorbates can be discharged by techniques known per se, such as, e.g., screw conveyors. This configuration of the equipment allows continuous process control. For this, it may be necessary for the carrier material likewise to be fed continuously. This can be carried out, e.g., by transporting the carrier material from an additional feed vessel 25, by air or gas supply or by means of a screw conveyor, directly to the desired point of entry on the spray tower. Detailed instructions with regard to the suitable point of entry of the carrier material have already been given earlier. The discharging of the process gas can be carried out as described in FIG. 1.

The present invention also includes products for plant protection comprising at least one absorbate according to the invention loaded with particular substances for use in plant protection compositions. The term "products for plant protection" is to be understood as meaning compositions which, in addition to at least one absorbate according to the invention, also comprise at least one additional component which is not bound to the carrier of the absorbate according to the invention. These include products which are suitable for preventing, controlling or combating attack by pests and/or for preventing, regulating and/or minimizing damage to or diseases of plants, wood or wood products which can occur during the growth, production, processing, storage, transportation or marketing and/or for regulating, minimizing or preventing the effects of insects, acarids or other pests on working animals which are fed with the plants. This includes compositions which are certainly for use as insect or plant growth regulators and also defoliants, desiccants, agents for regulating, weakening or preventing the premature putrefaction of fruit and substances for application to cereals, either before or after harvesting, in order to protect the harvested crop from damage during storage and transportation. Further details on the definition, nomenclature and characterization of products for plant protection can be taken from the manual "Pesticide Specifications", Manual on Development and Use of FAO and WHO Specifications for Pesticides, published by the World Health Organization (WHO) and Food and Agriculture Organization of the United States, Rome, 2002, ISBN 92-5-104857-6. The entire contents of this publication are hereby explicitly incorporated by reference herein.

The products for plant protection according to the invention can exist in the solid, liquid, oil or resin form or in the form of dispersions. They are preferably solid formulations for direct use, such as dustable powders (DP), powders for dry seed treatment (DS), granules (GR) or tablets for direct application (DT), solid formulations for dispersion, such as wettable powders (WP), water dispersible powders for seed treatment (WS), water dispersible granules (WG), water dispersible tablets (WT), emulsifiable granules (EG) or emulsifiable powders (EP), solid formulations for dissolution before application, such as water soluble powders (SP), water soluble powders for seed treatment (SS), water soluble granules (SG) or water soluble tablets (ST)

or liquid formulations, such as "aqueous suspension concentrates" (SC), "suspension concentrates for seed treatment" (FS), "oil-based suspension concentrates" (OD) or "aqueous suspoemulsions" (SE).

The abovementioned formulation forms and in particular the abbreviations used correspond to the internationally recognized usage. Details can be found in the manual "Pesticide Specifications", Manual on Development and Use of FAO and WHO Specifications for Pesticides, published by the World Health Organization (WHO) and the Food and Agriculture Organization of the United States, Rome, 2002, ISBN 92-5-104857-6, Appendix E. The entire contents of this publication and in particular of Appendix E are incorporated herein by reference.

WP and WG formulations are particularly preferred.

The products for plant protection according to the invention can, in addition to the absorbates according to the invention loaded with particular substances for use in plant protection compositions, comprise additional solid fillers, such as, e.g., natural calcium carbonate, clays or natural products, or additional auxiliaries, such as, e.g. biocides, thickeners, antifreeze agents or binders.

The products for plant protection according to the invention can be prepared by bringing at least one absorbate according to the invention, loaded with particular substances for use in plant protection compositions, into contact with at least one additional constituent of the products for plant protection. This can be carried out according to mixing processes known per se, such as, e.g., in tumbler mixers or pan mixers.

Measurement Methods

Determination of the Pore Volume Distribution

The term "micropore volume" is understood to mean, within the context of the present invention, the volume of the pores with a pore diameter from 0.4 nm to 2 nm. The micropore volume is determined by nitrogen adsorption according to DIN 66135 with the ASAP 2400 device, Micromeritics, according to the t-method. The evaluation is carried out volumetrically using the t curve according to Harkins-Jura. The test specimen has to be pretreated for the determination of the micropore volume. For this, the test specimen is predried at 105° C. for 24 h and subsequently outgassed under vacuum at 200° C. for a time of 1 h.

The term "meso and macropore volume" is understood to mean, within the context of the present invention, the pore volume which is formed from pores with a diameter between 3.6 nm and 100 nm. This volume is determined using mercury porosimetry according to DIN 66133 with the Autopore-IV 9500 mercury porosimeter from Micromeritics. For the calculation, the contact angle of the mercury is assumed to be 140° and the surface tension thereof is assumed to be 480 mN/m. The pretreatment of the test specimen is carried out analogously to that in the determination of the micropore volume.

The total pore volume is composed of the sum of the results of the micropore volume, determined by means of nitrogen adsorption, and of the meso/macropore volume, determined by means of mercury porosimetry, described above.

The calculation of the proportion of micropore volume (unit=[%]) is carried out as follows:

$$\text{Proportion of micropore volume} = \frac{\text{micropore volume}}{\text{micropore volume} + \text{meso/macropore volume}} \times 100$$

Determination of the DBP Absorption

The DBP absorption (DBP number), which is a measure of the absorbency of the precipitated silica, was determined according to the standard DIN 53601 as follows:

12.50 g of pulverulent or spherical silica with a moisture content of 0-10% (the moisture content is optionally adjusted by drying at 105° C. in a drying cabinet) are placed in the kneading chamber (item number 279061) of the Brabender absorptometer "E" (without damping of the output filter of the torque sensor). In the case of granules, the sieve fraction from 3.15 to 1 mm (stainless steel sieves from Retsch) is used (by gentle pressing of the granules with a plastic spatula through the sieve with a mesh size of 3.15 mm). Dibutyl phthalate is added dropwise to the mixture at ambient temperature at a rate of 4 ml/min using the "Brabender T 90/50 Dosimat" while continuously mixing (rotational speed of the kneader blades: 125 rev/min). Incorporation is carried out with only a low power demand and is followed using the digital display. Towards the end of the determination, the mixture becomes pasty, which is indicated by a steep rise in the power demand. When the display shows 600 digits (torque of 0.6 Nm), both the kneader and the DBP metering are switched off via an electrical contact. The synchronous motor for the feeding of DBP is coupled to a digital counter so that the DBP consumption in ml can be read off.

The DBP absorption was given in the unit [g/100 g] without decimal places and was calculated from the following formula:

$$DBP = \frac{C*D*100}{S} + F$$

with

DBP=DBP absorption in g/100 g

C=DBP consumption in ml

D=density of DBP in g/ml (1.047 g/ml at 20° C.)

S=starting weight of silica in g

F=correction factor according to moisture content correction table in g/100 g

The DBP absorption was defined for the anhydrous dried silica or silica gel. If hydrous preciptated silicas or silica gels are used, the correction factor F is to be taken into consideration in the calculation of the DBP absorption. This factor can be determined from the following correction table, e.g. a water content of the silica of 5.8% would mean an increase of 33 g/(100 g) for the DBP absorption. The moisture content of the silica was determined according to the method "Determination of the moisture content or of the loss on drying" described subsequently.

Moisture content correction table for dibutyl phthalate absorption (anhydrous)

| % Moisture Content | .% Moisture Content | | | | |
|---|---|---|---|---|---|
| | .0 | .2 | .4 | .6 | .8 |
| 0 | 0 | 2 | 4 | 5 | 7 |
| 1 | 9 | 10 | 12 | 13 | 15 |
| 2 | 16 | 18 | 19 | 20 | 22 |
| 3 | 23 | 24 | 26 | 27 | 28 |
| 4 | 28 | 29 | 29 | 30 | 31 |
| 5 | 31 | 32 | 32 | 33 | 33 |
| 6 | 34 | 34 | 35 | 35 | 36 |
| 7 | 36 | 37 | 38 | 38 | 39 |
| 8 | 39 | 40 | 40 | 41 | 41 |
| 9 | 42 | 43 | 43 | 44 | 44 |
| 10 | 45 | 45 | 46 | 46 | 47 |

Determination of the Moisture Content or of the Loss on Drying

The moisture content or even loss on drying (LD) of silicas were determined according to ISO 787 2 after drying at 105° C. for 2 hours. This loss on drying consisted predominantly of water.

10 g of the pulverulent, spherical or granular silica were weighed out exactly to 0.1 mg in a dry weighing bottle with a ground-glass lid (diameter 8 cm, height 3 cm) (starting weight S). The test specimen was dried with the lid open at 105±2° C. for 2 h in a drying cupboard. Subsequently, the weighing bottle was closed and cooled down to ambient temperature in a dessicator cabinet with silica gel as drying agent.

The weighing bottle was weighed accurately to 0.1 mg on a precision balance, in order to determine the final weight F. The moisture content (LD) is determined in % according to

LD(1−F/S)*100, where F=final weight in g and S=starting weight in g.

Determination of the Tapped Density

The tapped density was determined according to DIN EN ISO 787-11.

A defined amount of a test specimen was not sieved beforehand then poured into a graduated glass cylinder and subjected to a specific number of taps using a jolting volumeter. During the tapping, the test specimen becomes compressed. As a result of the investigation carried out, the tapped density was obtained.

The measurements were carried out on a jolting volumeter with a counter of STAV 2003 type from Engelsmann, Ludwigshafen.

A 250 ml glass cylinder was first tared on a precision balance. Subsequently, 200 ml of silica were poured into the tared measuring cylinder using a powder funnel so that no void spaces are formed. This was achieved by tilting and rotating the cylinder about its longitudinal axis during the pouring operation. Subsequently, the amount of test specimen is weighed accurately to 0.01 g. The cylinder was then gently rapped so that the surface of the silica in the cylinder was level. The measuring cylinder was put into the measuring cylinder holder of the jolting volumeter and tapped 1250 times. The volume of the tapped test specimen is read off accurately to 1 ml after a single jolting pass.

The tapped density D(t) was calculated as follows:

$D(t) = w*1000/V$

D(t): tapped density [g/l]

V: volume of the silica after tapping [ml]

w: weight of the silica [g]

The following examples serve exclusively to more fully explain the present invention but do not, however, limit it in any way.

Determination of the Density of the Liquid Particular Substance for Use in Plant Protection Compositions or of the Liquid Mixture of Particular Substances for Use in Plant Protection Compositions The determination was carried out using a density hydrometer according to DIN 12791, Part 3. The reference temperature is 20° C.

EXAMPLES

Sipernat 22 S with a micropore volume<2 nm of 0.02 ml/g and a meso/macropore volume of 3.6 nm-100 nm of 1.38 ml/g was used for the preparation of the active substance absorbates. This corresponded to a proportion of macropore volume of 1.43%. The DBP of the Sipernat 22 S used was 265 g/100 g.

Example 1

Preparation of an Active Substance Absorbate Suitable for Direct Use as WP or for Further Processing to Give WP or WG Chemicals:

| | |
|---|---|
| Sipernat 22 S | 200 g |
| Malathion (Fyfanon 96-97%, Cheminova) | 756.5 g |
| Berol 916 (Akzo Nobel) | 43.5 g |
| Empikol LZ (Albright & Wilson) | 43.5 g |

The wetting agent Berol 916, preheated to 50° C., was dissolved in the malathion with stirring. The density of the solution at 20° C. is 1.222 g/ml. The liquid solution, cooled down to ambient temperature, was fed from a feed vessel to a pressure-resistant static mixer into which compressed carbon dioxide was simultaneously metered. The conditions in the static mixer were chosen so that carbon dioxide is present in the supercritical condition (P=100 bar; T=32° C.). Liquid and $CO_2$ were intensively mixed with one another and some part of the supercritical gas dissolves in the liquid, producing a solution saturated with gas.

Finally, the solution saturated with gas is expanded in the spray tower via a high pressure nozzle. Dissolved carbon dioxide is present in the droplets formed by the nozzle and escapes abruptly from these droplets in the expansion to atmospheric pressure, further reducing the droplets in size. Sipernat 22 S, fluidized in a stream of $CO_2$ gas, is simultaneously metered as carrier right into this mist of very fine droplets. Turbulent flow around the high pressure nozzle ensured intensive contact between liquid droplets and Sipemat 22 S and the liquid was bonded to the carrier. The powder formed settled out in the spray tower and is discharged batchwise.

The active substance absorbate thus obtained, with a concentration by weight of particular substances (malathion+Berol 916) for use in plant protection compositions before standardization of $X_{before}$=80% and after standardization of $X_{stand.}$=76.6%, based on the total weight of the absorbate, had mixed into it mechanically the solid pulverulent dispersant Empikol LZ and, accordingly, a ready-for-use plant protection composition formulation was prepared.

Comparative Example

Preparation of an Active Substance Absorbate According to a Conventional Process of the State of the Art Chemicals:

| | |
|---|---|
| Sipernat 22 S | 31 g |
| Malathion (Fyfanon 96-97%, Cheminova) | 52.1 g |
| Berol 916 (Akzo Nobel) | 3.0 g |
| Empikol LZ (Albright & Wilson) | 3.0 g |

Sipemat 22 S and the dispersant Empikol LZ are placed, according to the amounts in the preceding list, in a 500 ml Quickfit glass stirring device with a precision bearing stirrer and briefly mixed. A solution of malathion and the wetting agent Berol 916, prepared according to Example 1, is added thereto dropwise inside 30 minutes with stirring, and stirring is carried out for a further 5 minutes. The absorbate obtained exhibited a of particular substances for use in plant protection compositions (malathion+Berol 916) of $X_{before}$=64%. This corresponds to a standardized content by weight of $X_{stand.}$=59.3%.

Increasing the amount of liquid added in the comparative example to the percentage given in Example 1 resulted, in this conventional process, in overloading of individual silica particles and accordingly in an agglomerated mixture which is very firmly stuck together and which cannot be used further. In contrast to this, flowable, superficially dry, agglomerated absorbate particles were obtained in Example 1 which are suitable for further processing or, according to the agglomerate size, for direct use as WP or WG.

The entire contents of German Application No. 102006002765.5 are incorporated herein by reference.

The invention claimed is:

1. An absorbate, comprising:
   at least one carrier material selected from the group consisting of a precipitated silica, a pyrogenic silica, a silica gel, a natural clay, a modified natural clay and a diatomaceous earth; and
   at least one particular substance for use in plant protection compositions or a mixture of substances comprising at least one particular substance for use in plant protection compositions;
   wherein the total amount of the particular substances for use in plant protection compositions, $X_{stand.}$, is 70% to 99%.

2. The absorbate according to claim 1, wherein the carrier material has a proportion of micropore volume, based on the total pore volume, of less than or equal to 10% by volume.

3. The absorbate according to claim 1, wherein the carrier material exhibits a di-butyl-phthalate absorption of greater than or equal to 150 g/100 g.

4. The absorbate according to claim 1, wherein the carrier material is a precipitated silica, a pyrogenic silica or a silica gel.

5. The absorbate according to claim 1, wherein the carrier material has a tapped density of less than 200 g/l.

6. The absorbate according to claim 1, wherein the carrier material has a tapped density of less than 150 g/l.

7. The absorbate according to claim 1, wherein the carrier material has a tapped density of less than 100 g/l.

8. The absorbate according to claim 1, wherein the proportion of the particular substance for use in plant protection compositions or, in mixtures of at least two of these substances, the total amount of these substances, $X_{stand.}$, is 75 to 95%.

9. The absorbate according to claim 1, comprising at least one particular substance for use in plant protection composition having a melting point of less than or equal to 80° C.

10. The absorbate according to claim 1, comprising at least one absorbed component that is an active substance for plant protection composition.

11. The absorbate according to claim 1, comprising at least one of the absorbed components that is an auxiliary for plant protection compositions.

12. The absorbate according to claim 1, which is a water dispersable granule or wettable powder formulation.

13. A process for making an absorbate of claim 1, comprising:
   providing a liquid in a feed vessel, wherein the liquid comprises at least one of (1) a liquid or molten particular substance for use in plant protection compositions and (2) a liquid or molten mixture of substances comprising at least one particular substance for use in plant protection compositions;
   mixing, partly dissolving, or both mixing and partly dissolving, a gas in the liquid to form a mixture;
   feeding the mixture to an expansion element;
   conveying the mixture through the expansion element to expand the mixture; and
   adding at least one solvent pulverulent carrier material to the expanded mixture.

14. The process as claimed in claim 13, wherein the mixing, partly dissolving or both mixing and partly dissolving is carried out under elevated pressure.

15. The process as claimed in claim 13, wherein the mixing, the partly dissolving or both the mixing and partly dissolving is carried out under super critical conditions.

16. The process as claimed in claim 13, wherein the mixing, the partly dissolving, or both the mixing and the partly dissolving is carrier out with $CO_2$ at a pressure of greater than 73.83 bar and a temperature of greater than 31.04° C.

17. The process as claimed in claim 13, wherein the mixing, the partly dissolving or both the mixing and the partly dissolving is carried out in at least one of a mixer and a pressurized vessel.

18. The process according to claim 13, wherein the carrier material has a proportion of micropore volume, based on the total pore volume of less than or equal to 10% by volume.

19. The process according to claim 13, wherein the carrier material has a di-butyl-phthalate absorption of $\geq 150$ g/100 g.

20. The process according to claim 13, wherein the carrier material is a precipitated silica, a pyrogenic silica or a silica gel.

21. The process according to claim 13, wherein the carrier material has a tapped density of less than 200 g/l.

22. The process according to claim 13, wherein the carrier material has a tapped density of less than 150 g/l.

23. The process according to claim 13, wherein the carrier material has a tapped density of less than 100 g/l.

24. An absorbate made by the process of claim 13.

25. A plant protection product comprising the absorbate according to claim 1.

26. The product according to claim 25, which is a wettable powder or a water dispersable granule formulation.

27. A process, comprising:
applying the absorbate according to claim 1 onto a plant.

28. The process as claimed in claim 13, wherein the mixture is at least one of a liquid/gas solution and a liquid/gas melt.

29. An absorbate, comprising:
at least one carrier material selected from the group consisting of a precipitated silica, a pyrogenic silica, a silica gel, a natural clay, a modified natural clay and a diatomaceous earth; and
at least one plant protection substance absorbed by the carrier material;
wherein the total amount of the plant protection substance absorbed by the absorbate is $X_{stand.}$ of 70-99% based on the total weight of the absorbed plant protection substance and the carrier material;
wherein:

$$X_{stand} = \frac{100}{\rho_{Fl} * \left(\frac{100}{X_{vor}} - 1\right) + 1} \quad \text{formula (I)}$$

with
$X_{stand.}$=amount by weight standardized with regard to a liquid density of 1.00 g/ml, in %,
$X_{before}$=amount by weight before standardization, in %,
$\rho_1$=density of the absorbed particular substance for use in plant protection compositions or of the mixture of particular substances for use in plant protection compositions, in g/ml;
Wherein the amount by weight before the standardization is calculated according to formula (II):

$$X_{before} = \frac{W_{1abs.}}{W_{abs.total}} * 100\% \quad \text{formula (II)}$$

with
$W_{1\ abs.}$=weight of the absorbed plant protection substance, in g,
$W_{abs.\ total}$=total weight of the absorbate, in g.

30. The absorbate according to claim 29, wherein $X_{stand.}$ is 75-95%.

* * * * *